(12) United States Patent
Lasater

(10) Patent No.: US 7,037,603 B2
(45) Date of Patent: May 2, 2006

(54) MATERIAL AND METHOD TO PREVENT LOW TEMPERATURE DEGRADATION OF ZIRCONIA IN BIOMEDICAL IMPLANTS

(75) Inventor: Brian J. Lasater, East Wenatchee, WA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 71 days.

(21) Appl. No.: 10/853,922

(22) Filed: May 25, 2004

(65) Prior Publication Data

US 2005/0266270 A1    Dec. 1, 2005

(51) Int. Cl.
B32B 15/04    (2006.01)
B32B 18/00    (2006.01)

(52) U.S. Cl. ............... 428/701; 428/472.1; 428/632; 428/633; 428/702

(58) Field of Classification Search ............... 428/660, 428/628, 629, 632, 633, 626, 457, 469, 472, 428/689, 472.1, 701, 702
See application file for complete search history.

(56) References Cited

U.S. PATENT DOCUMENTS

| 4,354,912 | A | * | 10/1982 | Friese ................. 204/426 |
| 4,414,282 | A |   | 11/1983 | McCollister et al. |
| 4,525,464 | A | * | 6/1985  | Claussen et al. ......... 501/103 |
| 4,536,203 | A |   | 8/1985  | Kramer |
| 4,587,225 | A |   | 5/1986  | Tsukuma et al. |
| 4,853,353 | A |   | 8/1989  | Whalen et al. |
| 5,021,307 | A |   | 6/1991  | Brow et al. |
| 5,104,738 | A |   | 4/1992  | Brow et al. |
| 5,648,302 | A |   | 7/1997  | Brow et al. |
| 5,693,580 | A |   | 12/1997 | Brow et al. |
| 5,820,989 | A |   | 10/1998 | Reed et al. |
| 5,827,572 | A | * | 10/1998 | Song et al. .............. 427/255.4 |
| 6,069,103 | A | * | 5/2000  | Kwon ................... 501/103 |
| 2004/0181270 | A1 | | 9/2004 | Jiang et al. |

OTHER PUBLICATIONS

Schubert, et al., Surface Stabilization of Y-TZP, British Ceramic Proceedings, 34 (Ceram. Surf. Surf. Treat.), pp. 157-160, ISSN 0268-4373, 1984, no month.
Lin, Crystallite Size and Microstrain of Thermally Aged Low-Ceria- and Low-Yttria-Doped Zirconia, J. Am. Ceram. Soc., 81 [4] 853-60 (1998), no month.

(Continued)

Primary Examiner—Michael E. Lavilla
(74) Attorney, Agent, or Firm—Gary D. Schnittgrund

(57) ABSTRACT

The invention is directed to a material and a method of producing the material that is unaffected by the low-temperature degradation, humidity-enhanced phase transformation typical of yttria-stabilized zirconia in general, as well as of yttria-stabilized tetragonal zirconia polycrystalline ceramic (Y-TZP). Because of the high fracture toughness and high mechanical strength, this class of materials is widely used, including as implants, such as for the packaging material for small implantable neural-muscular sensors and stimulators. The destructive phase transformation is eliminated by converting the surface to stable cubic or T-prime zirconia by post-densification thermal treatment in a cation-rich milieu.

7 Claims, 2 Drawing Sheets

OTHER PUBLICATIONS

Koh, Improved Low-Temperature Environmental Degradation of Yttria-Stabilized Tetragonal Zirconia Polycrystals by Surface Encapsulation, J. Am. Ceram. Soc., 82 [6] 1456-58 (1999), no month.

Piconi, Y-TZP Ceramics for Artificial Joint Replacements Biomaterials 19 (1998) 1489-1494, no month.

Ho, Dissolution of Yttrium Ions and Phase Transformation of 3Y-TZP Powder in Aqueous-Solution, J. Am. Ceram. Soc., 82 [6] 1614-16 (1999), no month.

Li, Phase Transformation in $Y_2O_3$-Partially-Stabilized $ZrO_2$ Polycrystals of Various Grain Sizes during Low-Temperature Aging in Water, J. Am. Ceram. Soc., 81 [10] 2687-91 (1998), no month.

Chung, Microstructure and Phase Stability of Yttria-Doped Tetragonal Zirconia Polycrystals Heat Treated in Nitrogen Atmosphere, J. Am. Ceram. Soc., 80 [10] 2607-12 (1997), no month.

* cited by examiner

//<br>
MATERIAL AND METHOD TO PREVENT LOW TEMPERATURE DEGRADATION OF ZIRCONIA IN BIOMEDICAL IMPLANTS

FIELD OF THE INVENTION

This invention relates to a material and a method of increasing the useful life of an yttria-stabilized zirconia structure when implanted in living tissue.

BACKGROUND OF THE INVENTION

One widely employed bioceramic is alumina, which is considered bioinert. The search for an ideal bioceramic has included alumina, hydroxyapatite, calcium phosphate, and other ceramics. The first use of aluminas for implants in orthopedics and dentistry was in the 1960's. They were later employed in hip prostheses as early as 1970. Since those early days the quality and performance of aluminas have improved. High-purity, high-density, fine-grained aluminas are currently used for a wide range of medical applications, e.g. dental implants, middle ear implants, and hip or knee prostheses.

Although the aluminas currently available perform satisfactorily, a further improvement in strength and toughness would increase the safety factor and may extend usage to higher stressed components. A proposed candidate to add to this list is stabilized-zirconia, because of its potential advantages over alumina of a lower Young's modulus, higher strength, and higher fracture toughness. Another advantage of stabilized-zirconia is low-wear residue and low coefficient of friction. Because, zirconia undergoes a destructive phase change at between 1000° and 1100° C., changing from monoclinic to tetragonal, phase stabilization admixtures of calcia, magnesia, ceria, yttria, or the like are required.

Tetragonal zirconia polycrystalline ceramic, commonly known as TZP, which typically contains 3 mole percent yttria, coupled with the small size of the particles, results in the metastable tetragonal state at room temperature. Under the action of a stress field in the vicinity of a crack, the metastable particles transform, with a 3% to 4% volume increase, by a shear-type reaction, to the monoclinic phase. Crack propagation is retarded by the transforming particles at the crack tip and by the compressive back stress on the crack walls behind the tip, due to volume expansion associated with transformation to the monoclinic phase.

The well-known transformation toughening mechanism is operative in zirconia ceramics whose composition and production are optimized such that most of the grains have the tetragonal crystal structure. These TZP ceramics, most notably their mechanical properties in air at room temperature, are superior to those of zirconia-toughened aluminas and to other classes of zirconias. While the biocompatibility of TZP ceramic has not been fully assessed, it has been preliminarily investigated.

For example, in one study by Thompson and Rawlings [see I. Thompson and R. D. Rawlings, "Mechanical Behavior of Zirconia and Zirconia-Toughened Alumina in a Simulated Body Environment," Biomaterials, 11 [7] 505–08 (1990)]. The result was that TZP demonstrated a significant strength decrement when aged for long periods in Ringer's solution and was therefore unsuitable as implant material.

Drummond [see J. L. Drummond, J. Amer. Ceram. Soc., 72 [4] 675–76 (1989)] reported that yttria-stabilized zirconia demonstrated low-temperature degradation at 37° C. with a significant decrement in strength in as short a period as 140 to 302 days in deionized water, saline, or Ringer's solution. He also reports on similar observation by others, where yttria-doped zirconia demonstrated a strength decrement in water vapor, room temperature water, Ringer's solution, hot water, boiling water, and post-in vivo aging.

TZP components suffer a decrement in strength properties after exposure for only a few days to humid environments. This degradation of mechanical properties occurs when moisture is present in any form, for example, as humidity or as a soaking solution for the TZP component. TZP components have been observed to spontaneously fall apart after times as short as a few weeks in room temperature water. This is of particular importance in living-tissue implanted devices that contain components made of this class of material. Long-term implantation of devices that contain yttria-stabilized (or partially-stabilized) zirconia components is not feasible with available materials.

One approach to preventing the low-temperature degradation of zirconia that was doped with 3 mole percent yttria is presented by Chung, et al. [see T. Chung, H. Song, G. Kim, and D. Kim, "Microstructure and Phase Stability of Yttria-Doped Tetragonal Zirconia Polycrystals Heat Treated in Nitrogen Atmosphere," J. Am. Ceram. Soc., 80 [10] 2607–12 (1997)]. The TZP sintered material was held for 2 hours at 1600° or 1700° C. in flowing nitrogen gas.

Analysis showed that the resulting surface consisted of cubic grains with tetragonal precipitates, while the interior was only slightly affected by the nitrogen exposure. Chung reported that low-temperature degradation was prevented because degradation of TZP started at the surface, which is protected from degradation by the stable cubic phase.

An alternate material and an easy to apply method of producing stable material to prevent the detrimental low-temperature phase change are needed.

DETAILED DESCRIPTION OF THE PREFERRED EMBODIMENT

A broadly applicable material and method of producing the material begins with the densified as-sintered, post-hot pressed, or hot isostatically pressed tetragonal zirconia polycrystalline ceramic (TZP) material that has been made by processes that are known to one skilled in the art, containing about 3 mole percent of yttria, which is subsequently thermally processed to convert the surface to a stable phase of cubic or T-prime zirconia (zirconium oxide) phase. It is well established that the cubic and T-prime phases of zirconia are stable in moist environments and are not subject to the deleterious low-temperature degradation failure mechanism that plagues TZP materials.

Figure 1:
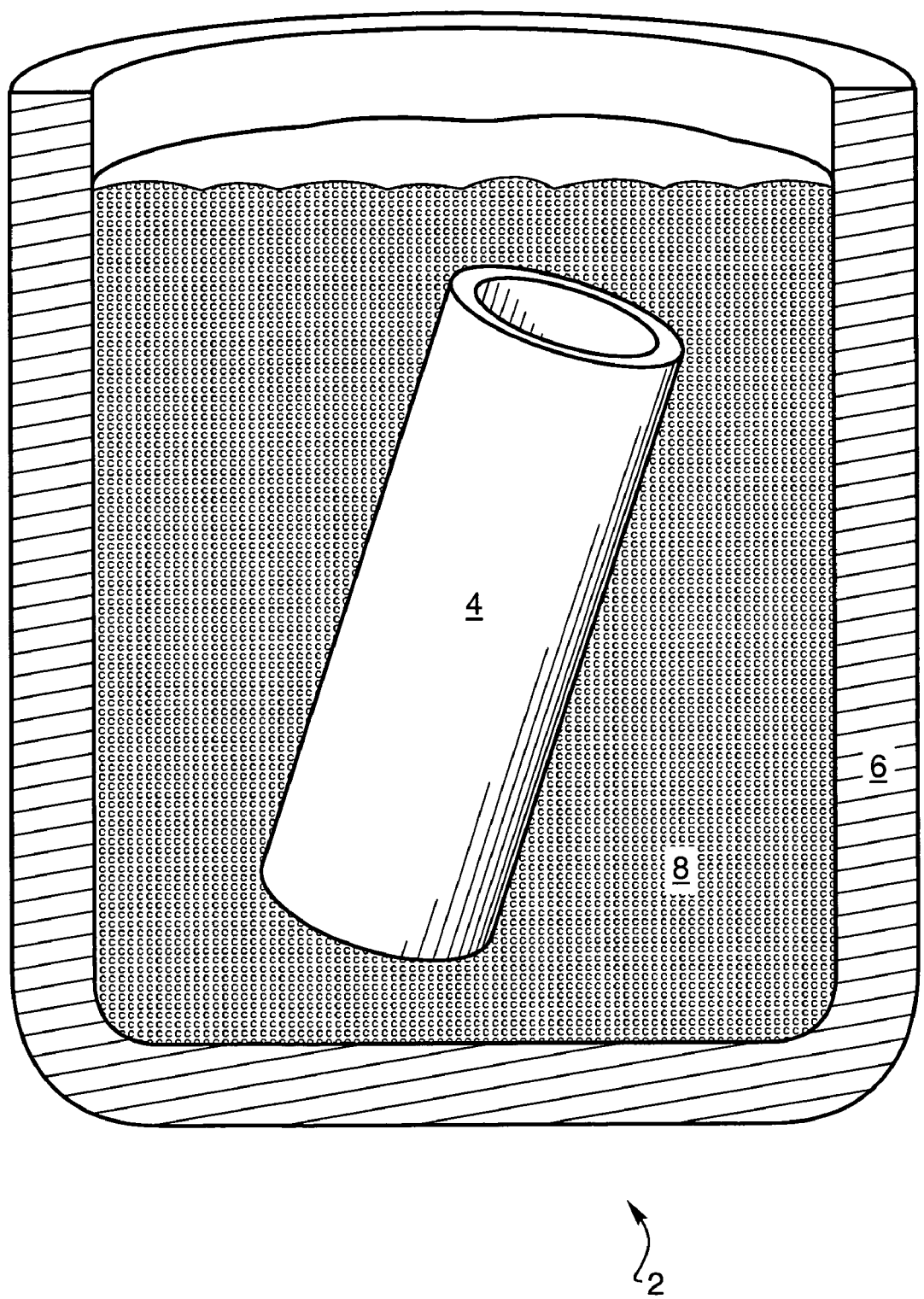
FIG. 1 presents a schematic representation of a ceramic component being thermally treated.

As presented in FIG. 1, a thermal treatment apparatus 2 is utilized to form the low-temperature resistant material. A densified ceramic component 4 comprised of TZP is placed in a containment vessel 6. A cation-rich bed 8 preferably comprised of a powder material surrounds the ceramic component 4.

The thermal treatment apparatus 2 is preferably placed in a furnace at one atmosphere pressure in an air environment and held at between 800° C. to 1500° C. for 15 to 90 minutes, and more preferably at 1100° C. to 1200° C. for 30 to 45 minutes. In alternative embodiments, the atmosphere may be an inert atmosphere, such as argon, or a reducing or vacuum atmosphere.

The cation-rich bed 8 is preferably substantially comprised of yttria, ceria, magnesia, or calcia. It is believed that the cation diffuses into the surface of the ceramic component and increases the molar percentage of stabilizing oxide from approximately 3 mole percent to about 10 mole percent. The conversion layer is preferably 0.1 to 10 microns deep, and more preferably 4 to 7 microns deep.

In an alternate embodiment, the ceramic component 4 is coated with 500 to 15,000 angstroms, and more preferably 5,000 to 10,000 angstroms, of a cation-rich layer of yttria, ceria, magnesia, or calcia. The coating is applied by methods known to one skilled in the art, such as chemical vapor deposition, physical vapor deposition, electron beam evaporation, ion beam assisted deposition; ion implantation, plasma spraying, sol-gel processing, or metallic plating followed by post-deposition oxidation or diffusion.

In yet another alternate embodiment, the thermal treatment apparatus 2 is operated absent the cation-rich bed 8, while the ceramic component 4 has been coated with the cation-rich layer, thus achieving the stable surface conversion to cubic or T-prime zirconia.

In another embodiment, the thermally treated ceramic component 2 having the stable cubic or T-prime surface layer is coated with a hermetic coating to further assure that the ceramic component 2 will remain stable and will not be subject to low-temperature degradation. The hermetic coating is comprised of known ceramic materials that are capable of forming a hermetic coating, including silica, alumina, silicon nitride, zirconia, silicon-oxynitride, aluminum oxynitride, silicon-aluminum oxynitride, and ultra-nanocrystalline diamond thin film. These ceramic coatings may be applied by combustion chemical vapor deposition, physical vapor deposition, electron beam evaporation, ion beam assisted deposition, ion implantation, or chemical vapor deposition.

The coating can be deposited at room temperature for combustion chemical vapor deposition, physical vapor deposition, electron beam evaporation, or ion beam assisted deposition.

Figure 2:
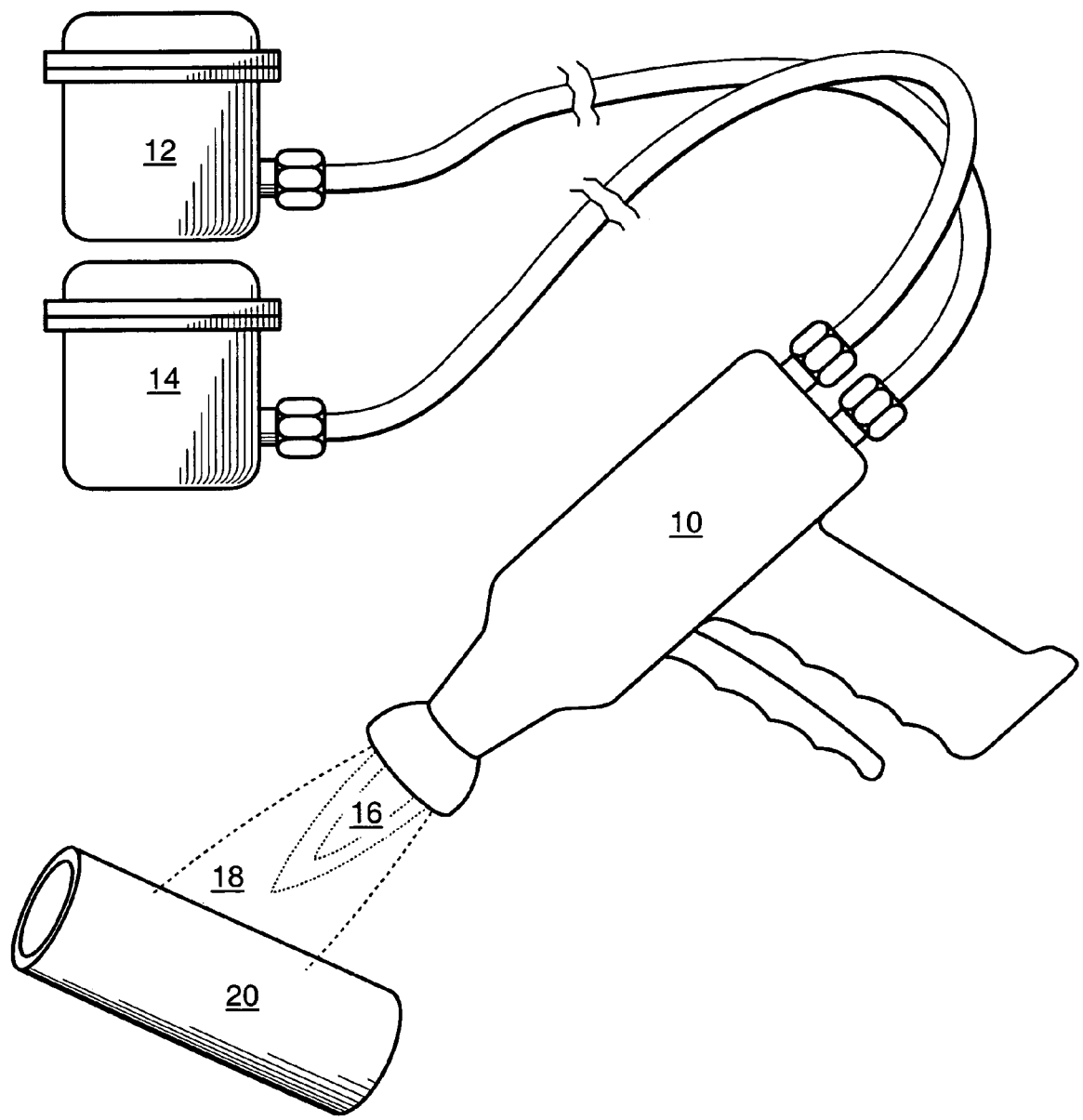
FIG. 2 presents a schematic representation of a combustion chemical vapor deposition process.

Chemical vapor deposition, known to those skilled in the art, is performed in a high temperature furnace. The furnace is heated to 800° to 1300° C. and chemical precursors are placed into the furnace in gaseous form. The gases dissociate in the heat and deposit on the substrate or part. Combustion chemical vapor deposition, illustrated in FIG. 2, does not employ a furnace and may be practiced in an air or inert gas milieu. Rather a combustion gun 10 is used in which a fuel 14 flows and ignites a very hot flame 16. Once the hot flame 16 is established, the precursor chemicals 12 are injected into the flame 16 with a similar end result as achieved with a classic chemical vapor deposition process, where the precursor chemical 12 is deposited on ceramic component 20.

Ion implantation is performed in a vacuum chamber with an ion gun and source of materials to be implanted. For example, one wanted to implant titanium into $ZrO_2$, a titanium target would be placed inside a vacuum chamber. Argon ions would bombard the titanium target and knock atoms off and ions which would be directed in a beam to impact the surface of the $ZrO_2$. The energy is sufficient to embed or implant the titanium atoms to a depth of about 0.1 microns. Thus there is no coating, per se, to flake off of the underlying substrate.

In addition to these hermetic ceramic coatings, other coatings that are known to those skilled in the art may be applied by known methods to create a hermetic coating on the TZP ceramic, where the coating protects from low-temperature degradation by virtue of keeping humidity and moisture isolated from the vulnerable TZP ceramic. Such coatings include polytetrafluoroethylene, silicone, or any biocompatible organic coating, such as parylene or liquid crystal polymer. Parylene, for example, is a vacuum deposited plastic film used to coat many types of substrates. Parylene coatings provide excellent corrosion resistance, barrier properties and exhibit superior dielectric protection.

The resulting coating is preferably 500 to 15,000 angstroms thick, and more preferably 5,000 to 10,000 angstroms thick.

In an alternate embodiment, the TZP ceramic is coated with a hermetic coating without first converting the surface to the stable cubic or T-prime phase.

An additional embodiment is to apply a glass or glass ceramic coating to the TZP where the glass coating is hermetic to moisture and is biocompatible. Examples of glass coating include Cabal 17, Babal-1d, Srbal-1, or TIG-24, which are known to those skilled in the art, see for example U.S. Pat. No. 5,021,307 to Brow, et al., U.S. Pat. No. 5,104,738 to Brow, et al., U.S. Pat. No. 5,648,302 to Brow, et al., and U.S. Pat. No. 5,693,580 to Brow, et al., each of which is incorporated by reference herein in its entirety. It is important that the selected glass or glass ceramic coating have a coefficient of thermal expansion that matches that of the TZP ceramic. See for example U.S. Pat. No. 4,414,282 to McCollister, et al., U.S. Pat. No. 4,536,203 to Kramer, and U.S. Pat. No. 5,820,989 to Reed, et al., each of which is incorporated by reference herein in its entirety. The preferred material is TIG-24.

The preferred deposition method for the glass or glass ceramic is to apply the material by spraying, painting, electrophoresis, physical vapor deposition, electron beam evaporation, ion beam assisted deposition or similar known processes for applying a thin hermetic coating to TZP ceramic.

Obviously, many modifications and variations of the present invention are possible in light of the above teachings. It is therefore to be understood that, within the scope of the appended claims, the invention may be practiced otherwise than as specifically described.

What is claimed is:

1. A densified low-temperature degradation resistant tetragonal zirconia polycrystal ceramic having an outer surface that is substantially comprised of a stable phase,
   said stable phase formed in situ by thermal treatment of said ceramic in the presence of a cation-rich material, wherein
   the outer surface is covered with a hermetic coating.

2. The ceramic of claim 1, wherein said hermetic coating is comprised of parylene.

3. The ceramic of claim 1, wherein said hermetic coating is comprised of liquid crystal polymer.

4. The ceramic of claim 1, wherein said hermetic coating is comprised of a glass ceramic.

5. A densified low-temperature degradation resistant tetraponal zirconia polycrystal ceramic having an outer surface that is substantially comprised of a stable phase,
said stable chase formed in situ by thermal treatment of said ceramic in the presence of a cation-rich material the outer surface is covered with a hermetic coating, wherein
said hermetic coating is comprised of ultra-nanocrystalline diamond.

6. A densified low-temperature degradation resistant tetragonal zirconia polycrystal ceramic having an outer surface that is substantially comprised of a stable phase, said stable phase formed in situ by thermal treatment of said ceramic in the presence of a cation-rich material, the outer surface is covered with a hermetic coating, wherein
said hermetic coating is comprised of a biocompatible glass.

7. The ceramic of claim 6, wherein said biocompatible glass is selected from the group consisting of Cabal 17, Babal-1d, Srbal-1, and TIG-24.

* * * * *